United States Patent [19]

Perregaard et al.

[11] Patent Number: 5,216,001
[45] Date of Patent: Jun. 1, 1993

[54] INDOLE DERIVATIVES

[75] Inventors: Jens K. Perregaard, Jaegerspris; Kim Andersen, Copenhagen; Klaus P. Boegesoe, Lyngby; Henrik Pedersen, Broenshoej, all of Denmark

[73] Assignee: H. Lunbeck A/S, Copenhagen-Valby, Denmark

[21] Appl. No.: 722,081

[22] Filed: Jun. 27, 1991

[30] Foreign Application Priority Data

Jul. 2, 1990 [DK] Denmark .................. 1585/90

[51] Int. Cl.$^5$ .................. C07D 401/14; C07D 403/14; C07D 403/04; A61K 31/445
[52] U.S. Cl. .................. 514/323; 514/228.2; 514/235.8; 514/253; 514/254; 514/316; 514/318; 514/333; 514/339; 544/61; 544/130; 544/295; 544/364; 544/369; 544/370; 544/373; 546/193; 546/201; 546/256; 546/257; 546/262; 546/273
[58] Field of Search ............... 546/193, 201, 256, 257, 546/262, 273; 544/58.4, 61, 98, 130, 295, 364, 309, 370, 371, 373; 514/228.2, 235.8, 253, 254, 316, 318, 323, 339, 333

[56] References Cited

U.S. PATENT DOCUMENTS

| | | | |
|---|---|---|---|
| 3,135,794 | 6/1964 | Archer | 544/373 |
| 4,358,456 | 11/1982 | Ward | 546/201 |
| 4,525,360 | 6/1985 | Perregaard | 546/206 |
| 4,684,650 | 8/1987 | Begeso | 544/367 |
| 4,710,500 | 12/1987 | Perregaard | 544/371 |

Primary Examiner—C. Warren Ivy
Assistant Examiner—Celia Chang
Attorney, Agent, or Firm—Darby & Darby

[57] ABSTRACT

Specific 6-substituted or 2-alkyl substituted indole or 2,3-dihydroindole compounds are provided, having long lasting serotonin activity with specific binding to 5-HT$_2$ receptors of the central nervous system. These compounds are suitable for therapeutic treatment of CNS disorders, such as anxiety, depression, sleep disturbances, migraine, negative symptoms of schizophrenia, and Parkinson's disease.

14 Claims, No Drawings

INDOLE DERIVATIVES

The present invention relates to novel 6-substituted and/or 2-alkyl substituted indole and 2,3-dihydroindole derivatives and their acid addition salts with pronounced and long lasting central serotonin (5-Hydroxytryptamine; 5 HT) activity with specific binding to 5-HT$_2$ receptors, to the beneficial use of these derivatives in the treatment of CNS disorders such as anxiety, depression, sleep disturbances, migraine, schizophrenia (treatment of the negative symptoms), and, Parkinson's disease with a low degree of undesired side effects and to pharmaceutical compositions thereof methods for their preparation.

The novel indole and 2,3-dihydroindole derivatives of the present invention are represented by the following formula:

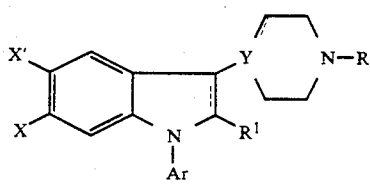

I.

where Ar is phenyl optionally substituted with one or more substituents selected from halogen, lower alkyl, lower alkoxy, hydroxy, trifluoromethyl, and cyano, or a hetero aromatic group preferably 2-thienyl, 3-thienyl, 2-furanyl, 3-furanyl, 2-oxazolyl, 2-imidazolyl, 2-pyridyl, 3-pyridyl, or 4-pyridyl;

the dotted line in the indole ring indicates an optional bond;

X is hydrogen, halogen, lower alkyl, lower alkoxy, hydroxy, lower alkylthio, lower alkylsulfonyl, lower alkyl- or dialkylamino, cyano, trifluoromethyl, or trifluoromethylthio;

X' is a substituent taken from the X-substituents above; or

X and X' are linked to constitute a 5-7 membered carbocyclic ring;

R$^1$ is hydrogen or lower alkyl optionally substituted with one or two hydroxy groups, provided that when X is hydrogen or fluoro, R$^1$ cannot be hydrogen;

Y is nitrogen or carbon;

when Y is carbon, the dotted line emanating from Y indicates an optional bond,

R is hydrogen, or lower alkyl, lower alkenyl, cycloalkyl, or cycloalkylmethyl, optionally substituted with one or two hydroxy groups, any hydroxy group present being optionally esterified with an aliphatic carboxylic acid having from two to twentyfour carbon atoms inclusive, or R is a group taken from structures 1a and 1b:

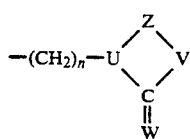

1a

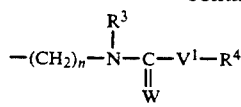

1b wherein n is an integer from 2-6, inclusive;

W is oxygen or sulfur;

U is nitrogen or carbon;

Z is —(CH$_2$)$_m$—, m being 2 or 3, or Z is —CH═CH— or Z is —COCH$_2$—, —CSCH$_2$—, or 1,2-phenylene optionally substituted with halogen or trifluoromethyl;

V is oxygen, sulfur, CH$_2$, —CH— or NR$^2$, wherein R$^2$ is hydrogen, lower alkyl or alkenyl lower optionally substituted with one or two hydroxy groups, or R$^2$ is a cycloalkyl or cycloalkylmethyl group;

V$^1$ is oxygen, sulfur, CH$_2$ or N—R$^5$, R$^5$ being defined as R$^2$ above;

R$^3$ is hydrogen, lower alkyl or alkenyl optionally substituted with one or two hydroxy groups, or a cycloalkyl group; and R$^4$ is one or two groups taken from the R$^3$-substituents.

Also the stereoisomers and prodrugs of the 6-substituted or 2-alkyl substituted 2,3-dihydroindole derivatives of formula I are embraced by this invention.

The terms lower alkyl, lower alkoxy, lower alkylthio and lower alkylsulfonyl designate such straight chained or banched groups having from one to four carbon atoms inclusive. Exemplary of such groups are methyl, ethyl, 1-propyl, 2-propyl, 1-butyl, 2-butyl, 2-methyl-2-propyl, 2-methyl-1-propyl, methoxy, ethoxy, 1-propoxy, 2-propoxy, methylthio, ethylthio, 1-propylthio, 2-propylthio, methylsulfonyl, ethylsulphonyl, or the like.

Cycloalkyl is such a group comprising 3-8 carbon atoms, inclusive.

Halogen means fluoro, chloro, bromo or iodo.

The acid addition salts of the invention are pharmaceutically acceptable salts of the compounds of Formula I formed with non-toxic acids. Exemplary of such organic salts are those with maleic, fumaric, benzoic, ascorbic, embonic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic and theophylline acetic acids, as well as the 8-halotheophyllines, for example 8-bromo-theophylline. Exemplary of such inorganic salts are those with hydrochloric, hydrobromic, sulfuric, sulfamic, phosphoric and nitric acids.

Prodrugs of the present invention may be conventional esters with available hydroxy groups, or in particular if the compound is a compound of the general formula I wherein W is oxygen and V is >NR$^2$, R$^2$ being hydrogen, the prodrug may be formed by acylating the nitrogenatom of the V group and being accordingly represented by the formula I wherein W is oxygen and V is >N—R$^{2'}$ wherein R$^{2'}$ designates a group

wherein A is O, S or NR$^a$ with R$^a$ being hydrogen, lower alkyl, or phenyl optionally substituted with one or more substituents selected from the group consisting of halogen, trifluoromethyl, lower alkyl, lower alkoxy, lower alkylthio and cyano;

B is a group $R^b$ which is alkyl or alkenyl containing from one to twentyfour carbon atoms inclusive, or cycloalkyl, optionally substituted with one or two hydroxy groups, phenyl optionally substituted with one or more substituents selected from the group consisting of halogen, trifluoromethyl, lower alkyl, lower alkoxy, lower alkylthio, or cyano; or B is $QR^{b'}$, wherein Q is O or S and $R^{b'}$ is one of the substituents defined for $R^b$ above; or B is $NR^cR^d$, wherein $R^c$ and $R^d$ independently are either hydrogen or one of the substituents defined for $R^b$ above.

Although the latter prodrugs are not esters, they have been found to decompose properly in order to release the compound of the invention over a desired prolonged period of time when administered parenterally as a depot formulation in an appropriate oil, such as peanut oil, sesame oil, cotton seed oil, corn oil, soy bean oil, olive oil, etc. or synthetic esters of fatty acids and glycerol or propylenglycol, e.g., viscoles ®.

Preferred embodiments of the invention are those indole derivatives wherein:

Ar is phenyl substituted with halogen, most preferably 4-fluorophenyl;

R is a group

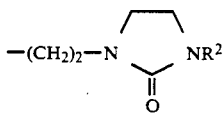

wherein $R^2$ is defined above, $R^2$ most preferably being hydrogen or isopropyl;

X is selected from —Cl, —Br, —$CF_3$, and —$CH_3$; and/or X' is H or Cl.

In another aspect the present invention provides a pharmaceutical preparation comprising at least one compound of the Formula I or a pharmaceutically acceptable acid addition salt or prodrug thereof as an active ingredient together with a pharmaceutically acceptable carrier or diluent.

In a further aspect the present invention provides the use of a compound of Formula I or a pharmaceutically acceptable acid addition salt or prodrug thereof for the manufacturing of a pharmaceutical preparation for the treatment of CNS disorders such as anxiety, depression, sleep disturbances, migraine, negative symptoms of schizophrenia, and Parkinson's disease (Parkinsonian syndrome).

The present invention also provides a method for treating CNS disorders comprising administration of a compound having the general Formula I or an acid addition salt thereof to a patient suffering from such a disease.

Finally, the present invention provides a method for the preparation of a derivative having the general Formula I, which method is described in the following.

Compounds, similar in structure to the derivatives of the present invention, are disclosed in our U.S. Pat. No. 4,710,500 (corresponding to EP patent No. 0200323) which discloses a general formula covering the corresponding 1-arylindoles optionally substituted in the benzo moiety of the indole ring system. Said compounds are stated to have potent and long lasting dopamine antagonistic and/or 5-$HT_2$ antagonistic activities.

However, though the 6-substituted 1-aryl indoles of the invention are included in the general formula of said U.S. patent, no compounds substituted in the 6-position have been specifically disclosed in the prior art. 2-Alkylated 1-aryl indoles are not covered by the general formula of said U.S. patent.

Surprisingly it has now been found that by introduction of certain substituents in the 6-position of the indole ring or by introduction of a lower alkyl group in the 2-position of the indole ring, dopaminergic (D-2) and noradrenergic ($\alpha_1$) blockade are practically absent, while these derivatives still are very potent and long lasting centrally acting 5-$HT_2$ antagonists. Even with a substituent left in the 5-position the indoles of the present invention have proven to be selective for the serotonergic system. Only a few compounds with this pharmacologically unique profile are known from the literature. Such compounds include ritanserin, seganserin, ICI 169369, ICI 170809, sergolexole and MDL 11939. These compounds belong to very diverse chemical structural classes. Ritanserin and seganserin are 4,4-diphenyl-methylene-1-heteroarylethyl substituted piperidines. The MDL compound is similarly a 4-phenylmethyl-1-phenylethyl piperidine derivative. The ICI compounds are 3-phenylquinoline derivatives whereas sergolexole belongs to the ergoline class of compounds. The indole and 2,3-dihydroindole derivatives of the present invention are very different in chemical structure from these known 5-$HT_2$ antagonist compounds.

Previously evidence of various clinical effects of 5-$HT_2$ antagonists have been presented. For example reference may be made to the following:

The selective 5-$HT_2$ antagonist ritanserin has been shown to be an antidepressant and to improve depressive symptoms of schizophrenia (E. Klieser, W. H. Strauss; Pharmacopsychiat. 21 (1988), pp. 391-393) and it has been demonstrated to exert effects in an animal test reminiscent of anxiolytic drug activity (F. C. Colpart et al.; Psychopharmacology (1985) 86; 303-305). Furthermore ritanserin has been shown to improve the quality of sleep (P. A. J. Janssen; Pharmacopsychiat. 21 (1988), 33-37).

Furthermore it is known that 5-HT is involved in migraine attacks. The links between 5-HT and migraine attacks are several and they suggest a number of mechanisms whereby 5-HT may be involved (Scrip Report; "Migraine—Current trends in research and treatment"; PJB Publications Ltd.; May 1991). Various 5-$HT_2$ antagonists are in clinical trials as anti-migraine agents, such as sergolexole (cf for example Pharma Projects, May 1991, 1359-1365). Studies of the serotonin and moderate dopamine receptor antagonist setoperone indicate that blockade of 5-$HT_2$ receptors may be related to improvement of negative symptoms of schizophrenia (Ceulemans et al., Psychopharmacology (1985) 85, 329-332).

Finally, ritanserin has been found to relieve neuroleptic-induced parkinsonism (Bersani et al.; Clinical Neuropharmacology, 13, No. 6 (1990, 500-506). Accordingly the potent and selective 5-$HT_2$ antagonists of the present invention are useful in the treatment of anxiety, depression, sleep disturbances, migraine, schizophrenia (treatment of the negative symptoms), and Parkinson's disease (Parkinsonian syndrome) substantially without causing neurological side effects.

The invention moreover relates to a method for the preparation of the novel 6-substituted or 2-alkylated indoles and 2,3-dihydroindoles of Formula I, which comprises a) reacting an indole derivative of the following formula:

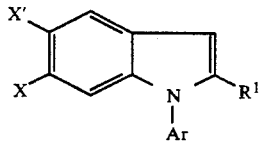
II.

wherein $R^1$, X, X' and Ar are as defined above, with a 4-piperidone of the formula:

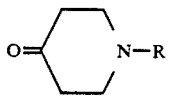
III wherein R is as defined above, or b) reducing the double bond in the tetrahydropyridyl ring of a compound of the formula:

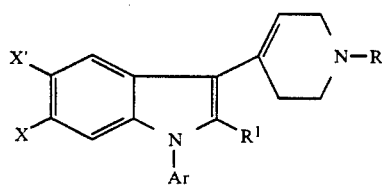
IV.

wherein $R^1$, X, X', Ar and R are as defined above, or c) reacting a compound of the following formula:

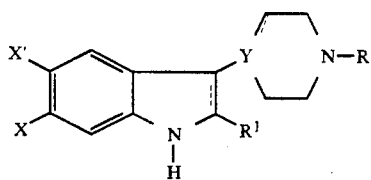
V.

wherein $R^1$, X, X', Y, R and the dotted lines are as defined above, with a compound of the formula:

Ar-hal    VI wherein Ar is as defined above and "hal" is halogen (Cl, Br or I) in the presence of a metal catalyst, or d) alkylating a compound of the following formula:

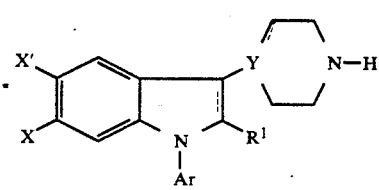
VII wherein $R^1$, X, X', Y, Ar and the dotted lines are as defined above with a lower alkyl halide, alkyl mesylate or tosylate, an epoxide of formula

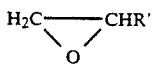

wherein R' is hydrogen, methyl or ethyl, or with a halide of the general formula:

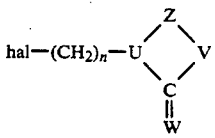
VIII a

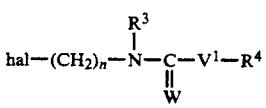
VIII b wherein U, Z, V, $V^1$, W, $R^3$, $R^4$ and n are as previously defined and "hal" is chloro, bromo or iodo, or e) reducing the carbonyl group in a compound of the following formula:

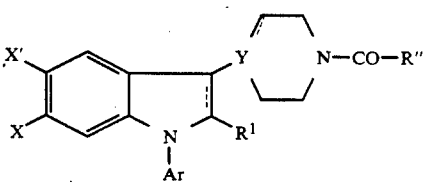
IX wherein $R^1$, X, X', Y, Ar and the dotted lines are as previously defined and R" is hydrogen, lower alkyl or lower alkoxy, or f) heating an indoxylester of the following formula:

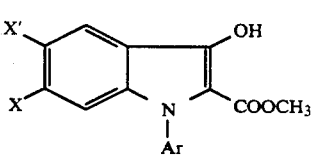
X wherein X, X' and Ar are as defined above, in the presence of an inorganic salt catalyst followed by continued heating in the presence of a piperazine derivative of formula:

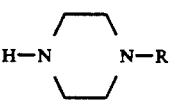
XI wherein R is as defined above, or g) reacting a 3-halogen substituted indole derivative of the formula XII with a piperazine derivative of the formula XIII:

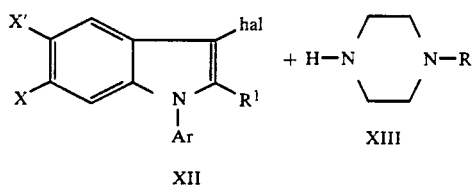 + 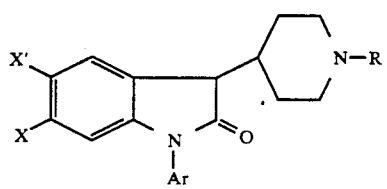

wherein $R^1$, X, X', Ar and R are as defined above and "hal" means chloro, bromo, or iodo, or h) reducing a 2-oxindole derivative of the following formula:

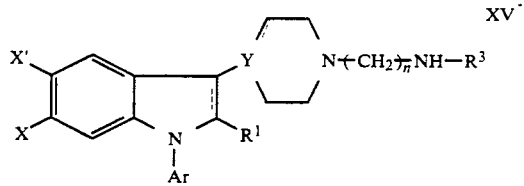

wherein X, X', Ar and R are as defined above, or i) acylating an aminoalkyl derivative of the following formula:

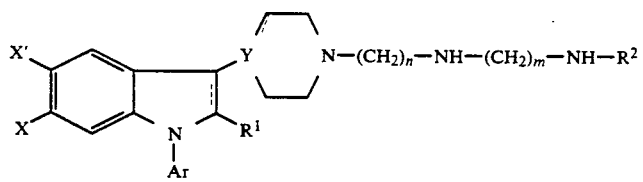

wherein $R^1$, X, X', Y, Ar, n, $R^3$ and the dotted lines are as defined above using a carboxylic acid halogenide, anhydride or mixed anhydride, a carbamyl or thiocarbamyl chloride, isocyanate, isothiocyanates or substituted chloroformate as acylating agent, or j) ringclosure reaction of an intermediate derivative of the following formula:

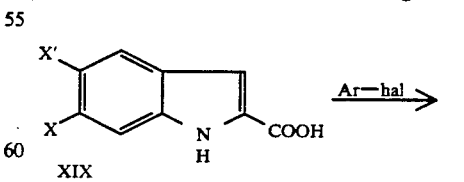

wherein $R^1$, X, X', Y, Ar, n, $R^2$, m and the dotted lines are as defined above, using urea, phosgene, thiophosgene or carbondisulfide to incorporate a carbonyl or thiocarbonyl group in the heterocyclic ring of structure Ia, or k) ringclosure reaction of an intermediate derivative of the following formula:

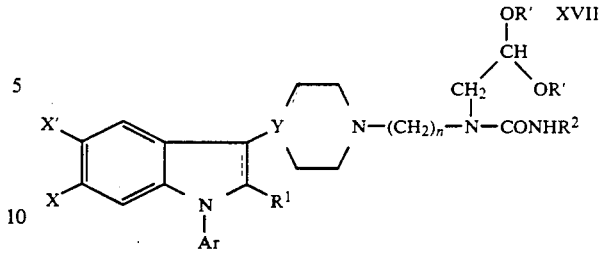

wherein $R^1$, X, X', Y, Ar, n, $R^2$ and the dotted lines are as defined above and R' is lower alkyl or alkenyl or constitute a ring by forming an ethylene or propylene bridge, or l) reducing the 2,3-double bond of a 3-piperidylindole of the following formula:

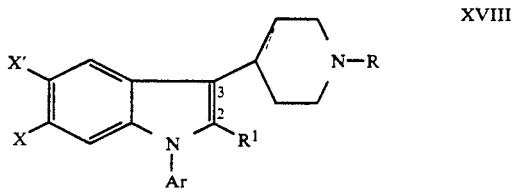

wherein $R^1$, X, X', Ar, R and the dotted line are as defined above, and then optionally converting the compound of formula I obtained into a pharmaceutically acceptable acid addition salt or prodrug thereof.

Preparation of the 2-unsubstituted intermediates and reaction conditions used in the methods a), b), c), d), e), f), and h) are described in detail in U.S. Pat. No. 4,710,500 and references cited therein for analogous compounds. The 2-Alkyl substituted 1-arylindoles (i.e. compounds having the structure II in which $R^1$ is not hydrogen) are readily available from the corresponding 2-carboxy-1-arylindoles XX which are prepared by Ullmann arylation of 2-carboxyindoles XIX (commercially available or prepared by the Japp-Klingemann procedure). 2-Methyl substituted indoles (IIa) were prepared as outlined in the following reaction scheme:

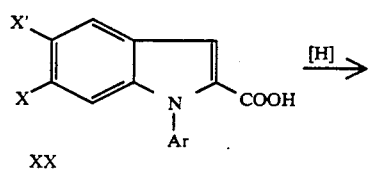

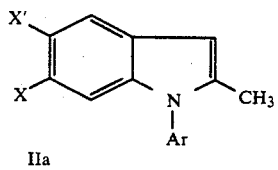

IIa

The Ullmann reaction procedure is reported in our U.S. Pat. No. 4,710,500. Reduction of the 2-carboxylic acid is conveniently performed in a two step sequence: 1) reduction with LiAlH$_4$ to the corresponding hydroxymethyl derivative, 2) catalytic hydrogenation to the methyl derivative IIa. 1-Aryl-3-haloindoles used in method g) are conveniently prepared from the corresponding 3-unsubstituted 1-arylindoles using N-chloro- or N-bromosuccinimide at room temperature preferably in a chlorinated solvent as e.g., dichloromethane, tetrachloromethane or 1,1,1-trichloroethane. This method is adapted for R. P. Mays et al., J. Heterocyclic Chem. 17, 1663–1664 (1980) and R. Sarges et al., J. Med. Chem. 32, 437–444 (1989). The substitution reaction with 1-alkylpiperazines of formula XIII is preferably performed at elevated temperatures (120°–200° C.) in aprotic polar solvents as e.g., N,N-dimethylformamide, hexamethylphosphoric triamide or N-methyl-2-pyrrolidone with K$_2$CO$_3$ as base and optionally copper or a copper (I) salt as Ullmann catalyst.

Aminoalkyl derivatives of the formula XV used in method i) as intermediates are conveniently prepared by alkylating the appropriate piperidyl-, 1,2,3,6-tetrahydropyridyl-or piperazinylindole derivative with an ω-halonitrile of the following formula: hal-(CH$_2$)$_{n-1}$CN in the presence of a free base (e.g., K$_2$CO$_3$ or triethylamine) in an inert solvent as acetone, methyl isobutyl ketone, or toluene at elevated temperatures (30°–100° C.). The cyano group may be reduced according to standard methods using e.g., AlH$_3$, LiAlH$_4$, B$_2$H$_6$ or a BH$_3$ complex. The R$^3$ substituent is introduced by direct alkylation or by an acylation/reduction procedure which is obvious to the chemist skilled in the art. Acylation of the thus-obtained aminoderivatives is accomplished by addition of an acylating agent at low temperatures (−20°–30° C.) preferably in chlorinated solvents (dichloromethane, chloroform, 1,1,1-trichloroethane) and, if needed to neutralize any acidic reaction products formed, in the presence of a base.

Ethylenediamines or propylenediamines having formula XVI used as intermediates for the ringclosure reaction in method j) are prepared by repeating with appropriate reagents the procedure described for the preparation of aminoalkyl derivatives in method i) using said aminoalkyl derivatives as starting materials. Generally heating (80°–150° C.) is required to effect ringclosure reactions with the appropriate carbonyl- or thiocarbonyl precursor compounds phosgene, thiophosgene, carbondisulfide, urea or thiourea).

Compounds XVII used in method k) as intermediates are prepared from structures XV wherein R$^3$ is H by monoalkylation with properly protected (ketalized) 2-haloacetaldehydes followed by addition of isocyanates to the secondary amine in an inert, chlorinated solvent as e.g., dichloromethane, chloroform or 1,1,1-trichloroethane at room temperature or slightly above.

The ringclosure of compounds XVII in method k) is effected by deprotection of the aldehyde under acidic reaction conditions at 0°–80° C. Potassium isocyanate serves as precursor for cyanuric acid under acidic conditions (trifluoroacetic or hydrochloric acid) for the preparation of 3-unsubstituted imidazol-2-on precursors.

Reduction of the 2,3-double bond of the indoles of structure XVIII in method I) is conveniently performed by catalytic hydrogenation at exhaustive reaction conditions, e.g., prolonged reaction times or high pressure, or by diborane reduction at elevated temperatures in an inert solvent such as dioxane or THF, or by reduction with NaBH$_4$ or NaCNBH$_3$ under suitable acidic reaction conditions (acetic acid, hydrochloric acid, or trifluoroacetic acid). Instead of 3-(4-piperidyl)-substituted indoles the corresponding 3-[4-(1,2,3,6-tetrahydro)pyridyl] substituted indoles may be intermediates for the 2,3-dihydroindole derivatives.

The ω-haloalkyl-2-imidazolidinone alkylating reagents (substructure of structure VIIIa) used in method d) were prepared according to modified literature procedures (see e.g., Johnston, T. P.: McCaleb, G. S.: Montgomery, J. A. The Synthesis of Antineoplastic Agents. XXXII. N-Nitrosureas. J. Med. Chem. 1963, 6, 669–681; Ebetino, F. F. Belg.Patent 653421, 1965; Chem.Abstr. 1966, 64, 12684; Costeli, J.; Züst, A. Ger.-Offen 2035370, 1971; Chem.Abstr. 1971, 74, 87985z). Other sidechains of structure VIIIa were prepared as stated in the literature.

When R$^2$ is a hydroxyalkyl substituent the hydroxy group may be introduced by deprotection of a labile ether derivative e.g., by acid induced decomposition, by hydrogenolysis, or by other methods obvious to the chemist skilled in the art.

6-Alkylthio substituted indoles or 2,3-dihydroindoles may also conveniently be prepared from the corresponding 6-alkylsulfone or 6-alkylsulfoxide substituted indoles or 2,3-dihydroindoles by reduction with proper reduction reagents such as LiAlH$_4$ and AlH$_3$ at reflux temperatures in inert high boiling solvents such as e.g., dioxan, dipropyl ether, dibutyl ether or diglyme.

The acid addition salts of the compounds of the invention are easily prepared by methods well known in the art. The base is reacted with either the calculated amount of organic or inorganic acid in an aqueous miscible solvent, such as acetone or ethanol, with isolation of the salt by concentration and cooling, or with an excess of the acid in an aqueous immiscible solvent such as ethyl ether or chloroform with the desired salt separating directly. Of course, these salts may also be prepared by the classical method of double decomposition of appropriate salts. The compounds of Formula I and the pharmaceutically acceptable acid addition salts thereof may be administered by any suitable route, for example orally in the form of tablets, capsules, powders, syrups, etc., or parenterally in the form of solutions for injection.

When the compound of Formula I exists as a prodrug thereof, it is suitably formulated as an injectable depot formulation in an appropriate pharmaceutically acceptable oil, such as peanut oil, sesame oil, cotton seed oil, corn oil, soy bean oil, olive oil, etc. or synthetic esters of fatty acids and glycerol or propylenglycol, e.g., Viscoleo ®.

Suitable pharmaceutical preparations may be prepared by methods well known in the art. Conveniently, the compounds of the invention are administered in unit dosage form containing said compound in an amount of about 0.10–100 mg, preferably about 1–50 mg. The total daily dose usually ranges from about 1.0 to 500 mg of the active compound of the invention.

In the following the invention is further illustrated by way of examples, which in no way may be construed as limiting for the invention.

EXAMPLE 1 (METHOD)

6-chloro-1-(4-fluorophenyl)-3-(1,2,3,6-tetrahydropyridin-4-yl)-1H-indole, hydrochloride, 1a 6-chloro-1-(4-fluorophenyl)-1H-indole (19 g) was dissolved in 150 ml of pre-heated acetic acid and added dropwise during ½ h to a solution of 4-piperidone hydrate hydrochloride (30 g) in a mixture of trifluoroacetic acid (200 ml) and acetic acid (100 ml) at gentle reflux. The mixture was heated for another 2 hours. After cooling to 50° C. and slow addition of 400 ml of acetone the hydrochloride salt of the title compound 1a precipitated. The salt was filtered off yielding 15.6 g. Mp 294°–295° C.

In a corresponding manner the following 3-(1,2,3,6-tetrahydropyridin-4-yl)-1H-indoles were prepared:

1-(4-fluorophenyl)-3-(1,2,3,6-tetrahydropyridin-4-yl)-6-trifluoromethyl-1H-indole, 1b, (oil)
1-(4-fluorophenyl)-6-methyl-3-(1,2,3,6-tetrahydropyridin-4-yl)-1H-indole, 1c, Mp: 262° C.
1-(4-fluorophenyl)-6-(2-propyl)-3-(1,2,3,6-tetrahydropyridin-4-yl)-1H-indole, 1d, (oil)
6-bromo-1-(4-fluorophenyl)-3-(1,2,3,6-tetrahydropyridin-4-yl)-1H-indole, 1e, Mp: 188°–191° C.
5,6-dichloro-1-(4-fluorophenyl)-3-(1,2,3,6-tetrahydropyridin-4-yl)-1H-indole, 1f, Mp: 196°–200° C.
6-cyano-1-(4-fluorophenyl)-3-(1,2,3,6-tetrahydropyridin-4-yl)-1H-indole, 1g, Mp: 139°–142° C.
1-(4-fluorophenyl)-3-(1,2,3,6-tetrahydropyridin-4-yl)-1,5,6,7-tetrahydrocyclo-pent[f]-1H-indole, 1h (oil)
1-(4-fluorophenyl)-6-methoxy-3-(1,2,3,6-tetrahydropyridin-4-yl)-1H-indole, 1i
1-(4-fluorophenyl)-6-methylsulfonyl-3-(1,2,3,6-tetrahydropyridin-4-yl)-1H-indole, 1j

EXAMPLE 2 (METHOD)

6-chloro-1-(4-fluorophenyl)-3-[1-[2-[3-(2-propyl)-2-imidazolidinon-1-yl]ethyl]-1,2,3,6-tetrahydropyridin-4-yl]-1H-indole, hydrobromide, 2a A mixture of compound 1a (10 g), 1-(2-chloroethyl)-3-(2-propyl)-2-imidazolidinon (6 g) (prepared according to the method of Ger. Offen. No. 2035370), potassium carbonate (10 g) and a KI crystal in methyl isobutyl ketone (200 ml) was refluxed overnight. The mixture was cooled to room temperature and water (500 ml) and ethyl acetate (200 ml) were added. The organic phase was separated, washed with brine (100 ml), dried (anh. MgSO₄) and finally the organic solvents were evaporated leaving the title compound 2a as an oil. A hydrobromide salt crystallized from acetone. Yield 4.8 g. Mp 243°–245° C.

In a corresponding manner the following N-alkylated 3-(1,2,3,6-tetrahydropyridin-4-yl)-1H-indoles were prepared:

1-(4-fluorophenyl)-6-methyl-3-[1-[2-[3-(2-propyl)-2-imidazolidinon-1-yl]ethyl]-1,2,3,6-tetrahydropyridin-4-yl]-1H-indole, 2b, Mp: 144° C.
5,6-dichloro-1-(4-fluorophenyl)-3-[1-[2-[3-(2-propyl)-2-imidazolidinon-1-yl]ethyl]-1,2,3,6-tetrahydropyridin-4-yl]-1H-indole, 2c, Mp: 108° C.
5,6-dichloro-1-(4-fluorophenyl)-3-[1-[2-(2-imidazolidinon-1-yl)ethyl]-1,2,3,6-tetrahydropyridin-4-yl]-1H-indole, 2d, Mp: 145°–148° C.
1-(4-fluorophenyl)-6-(2-propyl)-3-[1-[2-[3-(2-propyl)-2-imidazolidinon-1-yl]ethyl]-1,2,3,6-tetrahydropyridin-4-yl]-1H-indole, 2e (oil)
1-(4-fluorophenyl)-6-(2-propyl)-3-[1-[2-(2-imidazolidinon-1-yl)ethyl]-1,2,3,6-tetrahydropyridin-4-yl]-1H-indole, 2f (oil)
6-bromo-1-(4-fluorophenyl)-3-[1-[2-[3-(2-propyl)-2-imidazolidinon-1-yl]ethyl]-1,2,3,6-tetrahydropyridin-4-yl]-1H-indole, 2g (oil)
6-cyano-1-(4-fluorophenyl)-3-[1-[2-[3-(2-propyl)-2-imidazolidinon-1-yl]ethyl]-1,2,3,6-tetrahydropyridin-4-yl]-1H-indole, 2h, Mp: 137° C.
6-cyano-1-(4-fluorophenyl)-3-[2-(2-imidazolidinon-1-yl)ethyl]-1,2,3,6-tetra-hydropyridin-4-yl]-1H-indole, 2i, Mp: 146°–148° C.
1-(4-fluorophenyl)-3-[1-[2-[3-(2-propyl)-2-imidazolidinon-1-yl]ethyl]-1,2,3,6-tetrahydropyridin-4-yl]-1,5,6,7-tetrahydrocyclopent[f]-1H-indole, 2j (oil)
1-(4-fluorophenyl)-3-[1-[2-(2-imidazolidinon-1-yl)ethyl]-1,2,3,6-tetrahydropyridin-4-yl]-1,5,6,7-tetrahydrocyclopent[f]-1H-indole, 2 k (oil)
1-(4-fluorophenyl)-6-methylthio-3-[1-[2-[3-(2-propyl)-2-imidazolidinon-1-yl]ethyl]-1,2,3,6-tetrahydropyridin-4-yl]-1H-indole, 2l, MP: 148°–151° C.

EXAMPLE 3 (METHOD)

6-chloro-1-(4-fluorophenyl)-3-(4-piperidyl)-1H-indole, hydrochloride, 3a

Compound 1a (10 g) was added to 100 ml of NaOH solution and the base was subsequently extracted with dichloromethane (2×50 ml). The organic phase was dried (anh. MgSO₄) and the solvent evaporated. The remaining oil was dissolved in 100 ml of acetic acid and PtO₂ (300 mg) was added. The mixture was hydrogenated in a Parr apparatus for 5 hrs at 3 atm. The catalyst was then filtered off, and the acetic acid was evaporated. Dil. NaOH solution (200 ml) and ethyl acetate (200 ml) were added to the remaining oil. The organic phase was separated, dried (anh. MgSO₄) and ethyl acetate was evaporated leaving the crude title compound 3a as an oil. The hydrochloride salt crystallized from ethanol. Mp 268° C.

In a corresponding manner the following 3-(4-piperidyl)-1H-indoles were prepared:

6-bromo-1-(4-fluorophenyl)-3-(4-piperidyl)-1H-indole, 3b, Mp: 156°–158° C.
1-(4-fluorophenyl)-3-(4-piperidyl)-6-trifluoromethyl-1H-indole, hydrochloride, 3c Mp: 288°–291° C.
1-(4-fluorophenyl)-6-methyl-3-(4-piperidyl)-1H-indole, 3d (oil)
1-(4-fluorophenyl)-(6-methylsulfonyl)-3-[4-piperidyl]-1H-indole, 3e (oil)

EXAMPLE 4 (METHOD)

6-chloro-1-(4-fluorophenyl)-3-[1-[2-[3-(2-propyl)-2-imidazolidinon-1-yl]ethyl]-4-piperidyl]-1H-indole, 4a Compound 3a (60 g) was converted into the free base by extraction with dichloromethane (2×200 ml) from dil. NaOH solution (500 ml). The organic phase was dried (anh. MgSO₄), filtered and the solvent evaporated leaving the free base as an oil. The oil thus obtained was dissolved in methyl isobutyl ketone (800 ml) and 1-(2-chloroethyl)-3-(2-propyl)-2-imidazolidinon (35 g), potassium carbonate (50 g) and a KI crystal were added.

After refluxing overnight the mixture was filtered while still hot, methyl isobutyl ketone was evaporated and diethyl ether (400 ml) added. After stirring for ½ hour the precipitated product was filtered off. Finally recrystallization from ethanol yielded 56 g of pure title compound 4a. Mp: 134° C.

In a corresponding manner the following N-alkylated 3-(4-piperidyl)-1H-indoles were prepared:

6-chloro-1-(4-fluorophenyl)-3-[1-[2-(2-imidazolidinon-1yl)ethyl]-4-piperidyl]-1H-indole, 4b, Mp: 182° C.

1-(4-fluorophenyl)-3-[1-[2-[3-(2-propyl)-2-imidazolidinon-1-yl]ethyl]-4-piperidyl]-6-trifluoromethyl-1H-indole, oxalate, 4c, Mp: 139°–141° C.

1-(4-fluorophenyl)-3-[1-[2-(2-imidazolidinon-1-yl)ethyl]-4-piperidyl]-6-trifluoromethyl-1H-indole, 4d, Mp: 187°–188° C.

1-(4-fluorophenyl)-3-[1-[2-(2-pyrrolidinon-1-yl)ethyl]-4-piperidyl]-6-trifluoromethyl-1H-indole, fumarate, 4e, Mp: 168°–169° C.

6-chloro-1-(4-fluorophenyl)-3-[1-(2-hydroxyethyl)-4-piperidyl]-1H-indole, hydrochloride, 4f, Mp: 245°–249° C.

1-(4-fluorophenyl)-3-[1-[2-(2-imidazolidinon-1-yl)ethyl]-4-piperidyl]-6-methyl-1H-indole, 4g, Mp: 186°–188° C.

6-bromo-1-(4-fluorophenyl)-3-[1-[2-(2-imidazolidinon-1-yl)ethyl-]-4-piperidyl]-1H-indole, 4h, Mp: 178°–180° C.

1-(4-fluorophenyl)-6-methyoxy-3-[1-[2-[3-(2-propyl)-2-imidazolidinon-1-yl]ethyl]-4-piperidyl]-1H-indole, oxalate, 4i, Mp: 105°–107° C.

1-(4-fluorophenyl)-6-methoxy-3-[1-[2-(2-oxazolidinon-1-yl)ethyl]-4-piperidyl]-1H-indole, oxalate, 4j, Mp: 108°–110° C.

1-(4-fluorophenyl)-6-methylsulfonyl-3-[1-[2-[3-(2-propyl)-2-imidazolidinon-1-yl]ethyl]-4-piperidyl]-1H-indole, oxalate, 4k, Mp: 132°–136° C. 3-[1-[2-[3-(2-Benzyloxyethyl)-2-imidazolidinon-1yl]ethyl]-4-piperidyl]-6-chloro-1-(4-fluorophenyl)-1H-indole 4l, oil.

EXAMPLE 5 (METHOD)

1-(4-fluorophenyl)-6-methyl-3-[1-[2-[3-(2-propyl)-2-imidazolidinon-1-yl]ethyl]-4-piperidyl]-1H-indole, 5a The 3-(1,2,3,6-tetrahydropyridin-4-yl)-1H-indole derivative 2b (40 g) was dissolved in acetic acid (500 ml) and PtO$_2$ (2.4 g) was added. The mixture was hydrogenated in a Parr apparatus for 20 hrs at 3 atm. The catalyst was filtered off and ethyl acetate (500 ml) and ice (2 kg) were added. By addition of dil. NH$_4$OH pH was adjusted to >9. The organic phase was separated, dried (anh. MgSO$_4$), filtered and finally ethyl acetate was evaporated leaving 40 g of crude product. This product was dissolved in boiling acetone. By slowly cooling the title compound 5a crystallized yielding 19 g. Mp: 124° C.

In a corresponding manner the following N-alkylated 3-(4-piperidyl)-1H-indoles were prepared by catalytic reduction:

6-bromo-1-(4-fluorophenyl)-3-[1-[2-[3-(2-propyl)-2-imidazolidinon-1-yl]ethyl]-4-piperidyl]-1H-indole, 5b, Mp: 119° C.

1-(4-fluorophenyl)-6-(2-propyl)-3-[1-[2-[3-(2-propyl)-2-imidazolidinon-1-yl]ethyl]-4-piperidyl]-1H-indole, oxalate, 5c, Mp: 179°–180° C.

1-(4-fluorophenyl)-6-(2-propyl)-3-[1-[2-(2-imidazolidinon-1-yl)ethyl]-4-piperidyl]-1H-indole, 5d, Mp: 175°–177° C.

5,6-dichloro-1-(4-fluorophenyl)-3-[1-[2-[3-(2-propyl)-2-imidazolidinon-1-yl]ethyl]-4-piperidyl]-1H-indole, 5e, Mp: 141°–142° C.

5,6-dichloro-1-(4-fluorophenyl)-3-[1-[2-(2-imidazolidinon-1-yl)ethyl]-4-piperidyl]-1H-indole, 5f, Mp: 182°–183° C.

1-(4-fluorophenyl)-3-[1-[2-[3-(2-propyl)-2-imidazolidinon-1-yl]ethyl]-4-piperidyl]-1,5,6,7-tetrahydrocyclopent[f]-1H-indole, oxalate, 5g, Mp: 197° C.

1-(4-fluorophenyl)-3-[1-[2-(2-imidazolidinon-1-yl)ethyl]-4-piperidyl]-1,5,6,7-tetrahydrocyclopent[f]-1H-indole, 5h, Mp: 225°–228° C.

6-cyano-1-(4-fluorophenyl)-3-[1-[2-[3-(2-propyl)-2-imidazolidinon-1-yl]ethyl]-4-piperidyl]-1H-indole, 5i, Mp: 178° C.

6-cyano-1-(4-fluorophenyl)-3-[1-[2-(2-imidazolidinon-1-yl)ethyl]-4-piperidyl]-1H-indole, 5j, Mp: 175° C.

EXAMPLE 6 (METHOD)

6-chloro-1-(4-fluorophenyl)-3-[4-[2-[3-(2-propyl)-2-imidazolidinon-1-yl]ethyl]-1-piperazinyl]-1H-indole, 6a To 6-chloro-2-methoxycarbonyl-1-(4-fluorophenyl)-3-indolinon (7.5 g) in NMP (75 ml) was added MgCl$_2$, 6H$_2$O (9 g). The mixture was heated at 130° C. under N$_2$ for one hour and finally the temperature was raised to 190° C. while H$_2$O vapours were carried away by a gentle stream of N$_2$. 1-[2-[3-(2-propyl)-2-imidazolidinon-1-yl]ethyl]-piperazine (12 g) in NMP (30 ml) were added and the temperature kept at 190°–200° C. for another hour. After cooling to room temperature the reaction mixture was poured into ethyl acetate (200 ml) and a saturated NH$_4$Cl solution (500 ml) added. The organic phase was separated, dried (anh. MgSO$_4$), filtered and the solvent evaporated. The remaining oil was purified by column chromatography on silica gel (eluent ethyl acetate/ethanol/triethylamine 90/10/4) yielding 5.7 g of pure title compound 6a. Mp: 176°–177° C.

In a corresponding manner the following 3-(1-piperazinyl)-1H-indole derivatives were prepared:

1-(4-fluorophenyl)-6-methyl-3-[4-[2-[3-(2-propyl)-2-imidazolidinon-1-yl]ethyl]-1-piperazinyl]-1H-indole, dihydrochloride, 6b, Mp: 228° C.

6-chloro-1-(4-fluorophenyl)-3-[4-(2-hydroxyethyl)-1-piperazinyl]-1H-indole, 6c, Mp: 164°–165° C.

EXAMPLE 7 (INTERMEDIATES FOR METHOD)

3-[1-(2-aminoethyl)-4-piperidyl]-1-(4-fluorophenyl)-6-methyl-1H-indole, 7a

To a solution of the piperidyl compound 3d (16 g) in acetone (160 ml) were added triethylamine (4 ml) and chloroacetonitrile (4 ml). The mixture was refluxed for one hour and triethylamine (4 ml) and chloroacetonitrile (4 ml) were added once again. The mixture was then refluxed overnight, filtered and acetone was evaporated. The remaining oil was dissolved in ethyl acetate and filtered through silica gel (eluted with ethyl acetate). The compound with Rf value ~0.9 was collected yielding 6 g of 3-(1-cyanomethyl-4-piperidyl)-1-(4-fluorophenyl)-6-methyl-1H-indole. LiAlH$_4$ (2 g) was suspended in dry diethyl ether (60 ml) and the cyanomethyl derivative from above was dissolved in dry THF (100 ml) and added dropwise during 15 min. at 10°–15° C. The reaction mixture was then refluxed for 1.5 hours, cooled in an ice bath and excess LiAlH₄ was destroyed by cautious addition of a conc. NaOH solution (5 ml). Inorganic salts were filtered off and the solvents subsequently evaporated. The remaining oil was dissolved in dichloromethane, dried (anh. MgSO₄), filtered and dichloromethane was evaporated. The title compound 7a crystallized from diisopropyl ether. Mp: 101°–103° C.

In a corresponding manner the following 2-aminoethyl derivatives were prepared:
3-[1-(2-aminoethyl)-4-piperidyl]-6-chloro-1-(4-fluorophenyl)-1H-indole, 7b (oil)

EXAMPLE 8 (INTERMEDIATES FOR METHOD)

6-chloro-3-[1-(N-ethyl-2-aminoethyl)-4-piperidyl]-1-(4-fluorophenyl)-1H-indole, 8a (oil)

Compound 7b (31 g) was dissolved in dichloromethane (400 ml) and triethylamine (10 g) was added. Chloroacetyl chloride (9 g) dissolved in dichloromethane (100 ml) was added dropwise during 30 min. at 10°–15° C. The mixture was stirred for another hour at room temperature. Cold H₂O was added, the organic phase separated, dried (anh. MgSO₄), filtered and the solvent evaporated yielding 35 g of the crude chloroacetamide which was subsequently reduced by LiAlH₄ according to the method in Example 7 yielding 28 g of the title ethylamino compound 8a as an oil which was used in further synthesis without purification.

In a corresponding manner the following N-alkyl-2-aminoethyl derivatives were prepared:
6-chloro-1-(4-fluorophenyl)-3-[1-(N-methyl-2-aminoethyl)-4-piperidyl]-1H-indole, 8b (oil)

EXAMPLE 9 (METHOD)

1-(4-fluorophenyl)-3-[1-[2-[3-(2-propyl)-1-ureido]-1-ethyl]-4-piperidyl]-6-methyl-1H-indole, 9a The aminoethyl derivative 7a (3 g) was dissolved in dichloromethane (40 ml) and a solution of 2-propylisocyanate (1 ml) in dichloromethane (10 ml) was added dropwise at 30° C. during 15 min. The mixture was stirred for another hour. Dichloromethane was evaporated and the remaining oil was dissolved in diethyl ether. After ½ hour the precipitated title compound 9a was filtered off. Yield 1.8 g. Mp: 173°–174° C.

In a corresponding manner with intermediates from Examples 7 and 8 the following derivatives were prepared:
3-[1-[2-(3,3-dimethyl-1-ureido)-1-ethyl]-4-piperidyl]-1-(4-fluorophenyl)-6-methyl-1H-indole, oxalate, 9b, Mp: 161° C.
6-chloro-1-(4-fluorophenyl)-3-[1-[2-(3-methyl-1-thioureido)-1-ethyl]-4-piperidyl]-1H-indole, oxalate, 9c, Mp: 167°–170° C.
6-chloro-1-(4-fluorophenyl)-3-[1-[2-[1-ethyl-3-(2-propyl)-1-ureido]-1-ethyl]-4-piperidyl]-1H-indole, oxalate, 9d, Mp: 175°–176° C.
6-chloro-3-[1-[2-(3,3-dimethyl-1-ethyl-1-ureido)-1-ethyl]-4-piperidyl]-1-(4-fluorophenyl)-1H-indole, oxalate, 9e, Mp: 136°–138° C.
6-chloro-3-[1-[2-(3,3-dimethyl-1-thioureido)-1-ethyl]-4-piperidyl]-4-(4-fluoro-phenyl)-1H-indole, 9f, Mp: 129°–131° C.
6-chloro-1-(4-fluorophenyl)-3-[1-[2-[3-methyl-3-(2-propyl)-1-ureido]-1-ethyl]-4-piperidyl]-1H-indole, 9g, Mp: 118°–120° C.

6-chloro-1-(4-fluorophenyl)-3-[1-[2-(1,3-dimethyl-1-ureido)-1-ethyl]-4-piperidyl]-1H-indole, 9h, Mp: 106° C.
6-chloro-1-(4-fluorophenyl)-3-[1-[2-(1-methyl-3-(2-propyl)-1-ureido)-1-ethyl]-4-piperidyl]-1H-indole, 9i, Mp: 127° C.
3-[2-(2-acetylamino-1-ethyl)-4-piperidyl]-6-chloro-1-(4-fluorophenyl)-1H-indole, 9j, Mp: 150°–152° C.
6-chloro-3-[2-(2-ethyloxycarbonylamino-1-ethyl)-4-piperidyl]-1-(4-fluorophenyl)-1H-indole, 9k, Mp: 101°–103° C.
6-chloro-3-[1-[2-(3,3-dimethyl-1-ureido)-1-ethyl]-4-piperidyl]-1-(4-fluorophenyl)-1H-indole, hydrochloride, hemihydrate, 9l, Mp: 115°–116° C.

EXAMPLE 10 (INTERMEDIATE FOR METHOD)

6-chloro-1-(4-fluorophenyl)-3-[1-[N-[2-(2-propyl)aminoethyl]-2-aminoethyl]-4-piperidyl]-1H-indole, 10a To a solution in 1,1,1-trichloroethane (500 ml) of the intermediate chloroacetamide derivative (25 g) prepared as in Example 8 was added 2-propylamine (20 ml). The mixture was refluxed for 5 hrs. After cooling to room temperature, H₂O (1 L) was added, the organic phase separated, dried (anh. MgSO₄), filtered and volatile materials evaporated. The remaining oil was dissolved in dry THF and LiAlH₄ pellets (5 g) were added. The mixture was refluxed for 1.5 hours. After cooling in an ice bath H₂O/THF was added to destroy excess LiAlH₄. Inorganic salts were filtered off and THF evaporated leaving a crude product as an oil. The title compound 10a was purified by column chromatography on silica gel (eluted with methanol/ethyl acetate 1:1). Yield 15 g as an oil.

EXAMPLE 11 (INTERMEDIATE FOR METHOD)

3-[1-[N-(2-aminoethyl)-2-aminoethyl]-4-piperidyl]-6-chloro-1-(4-fluorophenyl)-1H-indole, 11a Compound 7b (10 g), triethylamine (3.5 g) and chloroacetonitrile (3 g) were heated at 50°–60° C. in 1,1,1-trichloroethane (100 ml) for 4 hrs. After cooling, dil. NH₄OH solution (200 ml) and ethyl acetate (100 ml) were added. The organic phase was separated, dried (anh. MgSO₄), filtered and the solvents were evaporated leaving 8.5 g of the crude aminoacetonitrile derivative as an oil. This crude product was added to a cooled solution of LiAlH₄ (3 g) and AlCl₃ (3 g) in dry diethyl ether (150 ml). The reaction mixture was refluxed for one hour. After cooling with an ice bath, a conc. NaOH solution (2–3 ml) was added cautiously. Inorganic salts were filtered off and subsequently extracted thoroughly by refluxing twice with dichloromethane. The combined organic phases were evaporated leaving the title compound 11a which was used without further purification. Yield 4.5 g

EXAMPLE 12 (METHOD)

6-chloro-1-(4-fluorophenyl)-3-[1-[2-(2-imidazolidinthion-1-yl)ethyl]-4-piperidyl]-1H-indole, 12a To a solution of compound 11a (4.5 g) in dichloromethane/methanol 1:1 (100 ml) was added 5 ml of carbondisulfide. The mixture was left at room temperature for one hour. Then the solvents were evaporated and finally the remaining viscous oil was heated at 130°–140° C. in solution in 1-pentanol. When the evolution of H₂S had ceased the solvents were evaporated. The resulting oil was purified by column chromatography on silica gel (eluted with ethyl acetate/methanol 1:1) yielding 2 g of the title compound 12a as a crystalline base. Mp: 184°–186° C.

EXAMPLE 13 (METHOD)

6-chloro-1-(4-fluorophenyl)-3-[1-[2-[3-(2-propyl)-2-imidazolidinthion-1-yl]ethyl]-4-piperidyl]-1H-indole, oxalate, 13a To a solution of compound 10a (2.2 g) and triethylamine (0.7 g) in 1,1,1-trichloroethane (50 ml) was added thiophosgene (0.6 g). The reaction mixture was slowly heated to reflux temperature. After gently refluxing for one hour the mixture was poured on ice and the organic phase was separated, dried (anh. MgSO$_4$), filtered and the solvent evaporated. The remaining oil was purified by column chromatography on silica gel (eluted with ethyl acetate/methanol 1:1) yielding the free base as an oil. The oxalate salt 13a crystallized from acetone. Yield 0.6 g. Mp: 154°–157° C.

EXAMPLE 14 (INTERMEDIATES FOR METHOD)

3-[1-[2-[3-(2-propyl)-2-imidazolidinon-1-yl]ethyl]-4-piperidyl]-6-methyl-1H-indole, 14a To a solution of potassium hydroxide (16 g) in methanol were added at 5° C. 4-piperidone hydrate hydrochloride (30 g) and a solution of 6-methyl-1H-indole (10 g) in methanol (50 ml). The mixture was refluxed for 16 hours. After cooling precipitated inorganic salts were filtered off. Methanol was evaporated and the remaining oil was dissolved in ethyl acetate (200 ml) and subsequently washed with brine (2×100 ml). After drying (anh. MgSO$_4$) the solvent was evaporated leaving 15 g of crude 6-methyl-3-(1,2,3,6-tetrahydro-4-pyridyl)-1H-indole, which was used without further purification. The pure tetrahydropyridyl derivative crystallized from diethyl ether. Mp: 150°–152° C. To a solution of 1-(2-chloroethyl)-3-(2-propyl)-2-imidazolidinon (32 g) in MIBK (500 ml) were added 6-methyl-3-(1,2,3,6-tetrahydro-4-pyridyl)-1H-indole (15 g), potassium carbonate (16 g) and potassium iodide (5 g). The mixture was refluxed for 19 hours and finally filtered while still hot. MIBK was evaporated and the resulting oil was dissolved in ethyl acetate (500 ml) and washed with brine (2×100 ml). After drying (anh. Na$_2$SO$_4$) ethyl acetate was evaporated. The remaining oil was stirred with diethyl ether (200 ml) and the precipitated, crystalline 3-[1-[2-[3-(2-propyl)-2-imidazolidinon-1-yl]ethyl]-1,2,3,6-tetrahydro-4-pyridyl]-6-methyl-1H-indole was filtered off. Yield: 14.5 g. Mp: 170°–174° C. To a solution of the thus prepared imidazolidinon derivative (14 g) in acetic acid (300 ml), was added PtO$_2$ (600 mg). This mixture was hydrogenated in a Parr apparatus at 3 atm. for 72 hours. The catalyst was filtered off and most of the acetic acid was evaporated in vacuo. The remaining oil was dissolved in H$_2$O and pH was adjusted to 9–10 by addition of dil. NaOH solution. The title compound 14a was extracted with dichloromethane (2×200 ml) and isolated as above. The crude product was purified by eluting (eluent:ethyl acetate/dichloromethane/ethanol/triethylamine (40:40:20:5) through silica gel. Yield: 4.5 g. Mp: 185° C.

In a corresponding manner were prepared:
3-[1-[2-[2-imidazolidinon-1-yl]ethyl]-4-piperidyl]-6-methyl-1H-indole, 14b Mp: 168°–170° C.

6-chloro-3-[1-[2-[3-(2-propyl)-2-imidazolidinon-1-yl]ethyl]-4-piperidyl]-1H-indole, 14c (used without purification)

6-chloro-3-[1-[2-[2-imidazolidinon-1-yl]ethyl]-4-piperidyl]-1H-indole, 14d (used without purification)

EXAMPLE 15 (METHOD)

3-[1-[2-[3-(2-(propyl)-2-imidazolidinon-1-yl]ethyl]-4-piperidyl]-6-methyl-1-phenyl-1H-indole, 15a To a solution of 3-[1-[2-[3-(2-propyl)-2-imidazolidinon-1-yl]ethyl]-4-piperidyl]-6-methyl-1H-indole 14a (3.7 g) in NMP (30 ml) were added iodobenzene (4 g), potassium carbonate (3.2 g), CuI (0.5 g) and ZnO (0.16 g). The mixture was heated under N$_2$ at 160° C. for 4.5 hours. After cooling to room temperature the mixture was poured into ethyl acetate (100 ml) and brine (100 ml). The organic phase was separated, dried (anh. MgSO$_4$) and ethyl acetate evaporated. The remaining oil (7 g) was purified by column chromatography (eluted with ethyl acetate/triethyl amine 100:4 on silica gel). The thus purified title compound 15a crystallized from diisopropyl ether. Yield: 2.0 g. Mp: 93° C.

In a corresponding manner were prepared the following derivatives by Ullmann arylation:

6-methyl-3-[1-[2-[3-(2-propyl)-2-imidazolidinon-1-yl]ethyl]-4-piperidyl]-1-(2-thie-nyl)-1H-indole, oxalate, 15b, Mp: 145° C.

6-methyl-3-[1-[2-[3-(2-propyl)-2-imidazolidinon-1-yl]ethyl]-4-piperidyl]-1-(3-thie-nyl)-1H-indole, oxalate, 15c, Mp: 134°–135° C.

1-(3-furanyl)-6-methyl-3-[1-[2-[3-(2-propyl)-2-imidazolidinon-1-yl]ethyl]-4-piperi-dyl]-1H-indole, oxalate, 15d, Mp: 83°–84° C.

6-methyl-3-[1-[2-[3-(2-propyl)-2-imidazolidinon-1-yl]ethyl]-4-piperidyl]-1-(4-pyri-dyl)-1H-indole, 15e, Mp: 144° C.

1-(2-fluorophenyl)-3-[1-[2-[3-(2-propyl)-2-imidazolidinon-1-yl]ethyl]-4-piperidyl]-6-methyl-1H-indole, oxalate, 15f, Mp: 150°–152° C.

1-(3-fluorophenyl)-3-[1-[2-[3-(2-propyl)-2-imidazolidinon-1-yl]ethyl]-4-piperidyl]-6-methyl-1H-indole, oxalate, 15g, Mp: 133°–135° C.

1-(4-chlorophenyl)-3-[1-[2-[3-(2-propyl)-2-imidazolidinon-1-yl]ethyl]-4-piperidyl]-6-methyl-1H-indole, oxalate, 15h, Mp: 178° C.

3-[1-[2-[3-(2-propyl)-2-imidazolidinon-1-yl]ethyl]-4-piperidyl]-6-methyl-1-(3-trifluoromethylphenyl)-1H-indole, oxalate, 15i, Mp: 97° C.

6-chloro-1-(2-fluorophenyl)-3-[1-[2-[3-(2-propyl)-2-imidazolidinon-1-yl]ethyl]-4-piperidyl]-1H-indole, 1½ oxalate, 15j, Mp: 106°–109° C.

6-chloro-1-phenyl-3-[1-[2-[3-(2-propyl)-2-imidazolidinon-1-yl]ethyl]-4-piperidyl]-1H-indole, 15k, Mp: 100° C.

3-[1-[2-[2-imidazolidinon-1-yl]ethyl]-4-piperidyl]-6-methyl-1-(4-pyridyl)-1H-indole, 15l, Mp: 141°–143° C.

6-chloro-3-[1-[2-[2-imidazolidinon-1-yl]ethyl]-4-piperidyl]-1-phenyl-1H-indole, 15m, Mp: 168° C.

EXAMPLE 16 (INTERMEDIATE FOR METHOD)

6-chloro-1-(4-fluorophenyl)-3-[1-[2-[1-(1,1-dimethoxy-2-ethyl)-3-(2-propyl)-1-ureido]-1-ethyl]-4-piperidyl]-1H-indole, 16a To a solution of 3-[1-(2-aminoethyl)-4-piperidyl]-6-chloro-1-(4-fluorophenyl)-1H-indole 7b (11 g) in dioxan (100 ml) were added 2-bromo-1,1-dimethoxyethane (5.6 g), potassium carbonate (5 g) and a potassium iodide crystal. The mixture was refluxed for 16 hours. After cooling, inorganic salts were filtered off and dioxan evaporated leaving crude 6-chloro-3-[1-[N-(1,1-dimethoxyethyl)-aminoethyl]-4-piperidyl]-1-(4-fluorophenyl)-1H-indole as an oil. The crude product was purified by column chromatography on silica gel (eluted with ethyl acetate/methanol 1:1). Yield: 6 g as an oil. The thus obtained alkylated aminoderivative (6 g) was dissolved in dichloromethane (100 ml) and 2-propylisocyanate (1.1 g) was added. After refluxing for 2 hours dichloromethane was evaporated and the title compound 16a was purified by column chromatography on silica gel (eluted with ethyl acetate/methanol 1:1). Yield: 4.9 g as an oil.

EXAMPLE 17 (METHOD)

6-chloro-1-(4-fluorophenyl)-3-[1-[2-[3-(2-propyl-)imidazol-2-on-1-yl]ethyl]-4-piperidyl]-1H-indole,hydrochloride, 17a To a solution of 6-chloro-1-(4-fluorophenyl)-3-[1-[2-[1-(1,1-dimethoxy-2-ethyl)-3-(2-propyl)-1-ureido]-1-ethyl]-4-piperidyl]-1H-indole 16a (4.9 g) in ethanol (50 ml) was added 3M aqueous hydrochloric acid (3 ml). The mixture was left for 3 days at room temperature and the solvents were subsequently evaporated. The title compound 17a crystallized as the hydrochloride from acetone. Yield: 1.3 g. Mp: 216°–218° C.

EXAMPLE 18 (METHOD VARIANT)

6-chloro-1(4-fluorophenyl)-3-[1-[2-[3-(2-hydroxyethyl)-2-imidazolidinon-1-yl]e-thyl]-4-piperidyl]-1H-indole, fumarate 18a A solution of 41 (4.3 g) in 6M hydrochloric acid (80 ml) was refluxed for 45 minutes. The solution was cooled and made alkaline with sodium hydroxide solution, and was extracted with dichloromethane. Conventional work-up of the organic phase yielded 3.3 g of the title compound as an oil which crystallized with fumaric acid from ethanol. Mp: 128°–130° C.

EXAMPLE 19

1-(4-fluorophenyl)-6-methylthio-3-[1-[2-[3-(2-propyl)-2-imidazolidinon-1-yl]ethyl]-4-piperidyl]-1H-indole, oxalate, 19a To a solution of 1-(4-fluorophenyl)-(6-methylsulfonyl)-3-[4-piperidyl]-1H-indole 3e (11 g) in a mixture of di-(n-butyl)ether (500 ml) and THF (100 ml) was added lithium aluminum hydride (5.6 g). The mixture was refluxed for 24 h and after cooling to room temperature THF (1000 ml) was added. Finally a 10% solution of water in THF (500 ml) was added with ice cooling. The solid was filtered off and the solvents were evaporated. Solution of the remaining oil in dichloromethane followed by drying and evaporation of the solvent afforded an oil (9.4 g) which contained 1-(4-fluorophenyl)-(6-methylthio)-3-(4-piperidyl)-1H-indole. A mixture of the thus obtained crude reduction product (9.4 g), 1-(2-chloroethyl)-3-(2-propyl)-2-imidazolidinon (7.6 g), potassium carbonate (7.6 g), a KI crystal and methyl isobutyl ketone (500 ml) was refluxed overnight. The reaction mixture was then cooled, poured into water (500 ml) and extracted with ethyl acetate (2×200 ml). The combined organic phases were washed with brine and dried (Na2SO4) and the solvents were evaporated in vacuo. The remaining oil was purified by column chromatography on silica gel (eluted with ethyl acetate/heptane 3:1 containing 4% triethyl amine). The title compound 19a was finally precipitated as its oxalate salt from ethanol. Yield: 0.09 g Mp: 105°–110° C.

EXAMPLE 20 (METHOD)

1-(4-fluorophenyl)-6-methyl-3-[1-[2-[3-(2-propyl)-2-imidazolidinon-1-yl]ethyl]-4-piperidyl]-2,3-dihydro-1H-indole, dioxalate, 20a The remaining oil (19 g) after crystallization of 1-(4-fluorophenyl)-6-methyl-3-[1-[2-[3-(2-propyl)-2-imidazolidinon-1-yl]ethyl]-4-piperidyl]-1H-indole, 5a in exam-ple 5 was purified by preparative HPLC chromatography (eluted with ethyl acetate/triethylamine 100:4) yielding 3.5 g of the title compound as an oil. The dioxalate salt 20a crystallized from acetone. Yield: 2.8 g. Mp: 85°–89° C.

EXAMPLE 21 (METHOD)

6-chloro-1-(4-fluorophenyl)-3-[1-[2-[3-(2-propyl)-2-imidazolidinon-1-yl]ethyl]-4-piperidyl]-2,3-dihydro-1H-indole, oxalate 21a To a solution of 6-chloro-1-(4-fluorophenyl)-3-[1-[2-[3-(2-propyl)-2-imidazolidinon-1-yl]ethyl]-4-piperidyl]-1H-indole 4a (2 g) in trifluoroacetic acid (15 ml) was added sodiumcyanoborohydride (1 g). After 2 h reaction at room temperature the solvent was evaporated in vacuo and ethyl acetate (50 ml) was added. The solution was washed twice with aqueous 2N sodium hydroxide (50 ml), dried (anh. Na2SO4) and the solvent was evaporated in vacuo. The crude product was purified by column chromatography on silica gel (eluted with ethyl acetate/heptane 3:1 containing 4% triethyl amine). The title compound was finally precipitated as its oxalate salt from acetone. Yield: 0.5 g Mp: 91°–100° C.

EXAMPLE 22 (INTERMEDIATE FOR COMPOUND 41)

1-(2-Benzyloxyethyl)-3-(2-chloroethyl)-2-imidazolidinon, 22a

To 3-benzyloxypropionic acid (129.6 g) in ether (310 ml) and N,N-dimethylformamide (4 ml) was added thionyl chloride (155 ml). The solution was refluxed for 2 hours, and solvents and excess thionyl chloride were removed by evaporation in vacuo. Yield 132 g of 3-Benzyloxypropionic acid chloride as an oil. To an ice cooled solution of the thus prepared acid chloride (132 g) in acetone (450 ml) was added a cold solution of sodium azide (48.5 g) in water (200 ml) at 5° C. After additional stirring at 5° C. for 30 minutes, the mixture was poured into water and toluene, and the aqueous phase was extracted twice with toluene. The combined organic phases were washed with brine. After drying (magnesium sulfate) the solution was heated slowly to 85° C. on a steam bath until evolution of nitrogen ceased. The solvent was removed in vacuo leaving 108.4 g of 2-benzyloxyethylisocyanate as an oil. A mixture of 2-benzyloxy-ethylisocyanate (10 g) and diethanolamine (5.72 g) in dichloromethane (60 ml) was refluxed for 2.5 hours. After cooling to room temperature, the solution was washed with brine. Drying (magnesium sulfate) and evaporation of the solvent yielded 11.4 g of N-(2-benzyloxyethyl)-N',N'-di-(2-hydroxyethyl)-urea as an oil. A solution of the urea derivative (11.4 g) in dichloromethane (55 ml) was cooled to 5° C., and thionyl chloride (8.3 ml) was added at a temperature below 10° C. After the addition the mixture was refluxed for 1 hour and then left over night at room temperature. The solution was washed with cold sodium hydrogen carbonate solution and saturated sodium chloride solution, dried over magnesium sulfate and evaporated in vacuo. The residue was dissolved in 1,1,1-trichloroethane and refluxed for 3 hours. After cooling the solution was washed with sodium hydrogen carbonate solution, dried over magnesium sulfate and evaporated in vacuo, yielding 6.6 g of the title compound 22a as an oil.

EXAMPLE 23 (INTERMEDIATE FOR METHOD 2-ALKYLATED 1-ARYLINDOLES)

1-(4-fluorophenyl)-2-methyl-1H-indole, 23a

To a solution of 2-carboxy-1H-indole (50 g) in DMF (600 ml) were added potassium hydroxide (40 g) and 4-fluoroiodobenzene (90 g). Reflux in an inert $N_2$ stream for 6 hours. $H_2O$/DMF was distilled off to obtain a constant boiling point of 148° C. After cooling to room temperature, ether (500 ml) was added. The precipitated material was filtered off and water (500 ml) was added. Undissolved material was filtered off. To the alkaline water phase was added ethyl acetate (500 ml) and pH was adjusted to 2 by addition of dil. aqueous HCl. The organic phase was worked up as yielding 2-carboxy-1-(4-fluorophenyl)-1H-indole (41 g) which melted at 213° C. The thus obtained carboxyindole (38 g) was added cautiously to a suspension of $LiAlH_4$ (7.5 g) in dry THF (350 ml) at such a rate that the temperature was kept below 50° C. The mixture was finally stirred at 50° C. for 1.5 h. After cooling 5M NaOH solution was added under vigorous stirring. Precipitated inorganic material was filtered off and washed thoroughly with dichloromethane. After evaporation of the combined organic phases 1-(4-fluorophenyl)-2-hydroxymethyl-1H-indole (35 g) was isolated as a crystalline product. Mp: 65°-66° C. The hydroxymethyl derivative (35 g) was dissolved in ethanol (600 ml). The solution was hydrogenated in a Parr apparatus with 15% Pd/C as catalyst at 3 ato. for 20 h. The catalyst was filtered off and ethanol evaporated leaving the crude title compound 23a as an oil. Purification by elution (dichloromethane/heptane 1:1 as eluent) through silica gel afforded the pure 1-(4-fluorophenyl)-2-methyl-1H-indole (18 g) as a crystalline product. Mp: 43° C.

EXAMPLE 24

From compound 23a was prepared the following 2-methylindoles by methods a), b) and d):
1-(4-fluorophenyl)-2-methyl-3-(1,2,3,6-tetrahydropyridin-4-yl)-1H-indole, 24a, oil 1-(4-fluoropheyl)-3-[1-[2-(2-imidazolidinon-1-yl)ethyl]-1,2,3,6tetrahydropyridin-4-yl]-2-methyl-1H-indole, 24b, Mp: 172°-177° C.
1-(4-fluorophenyl)-3-[1-[2-(2-imidazolidinon-1-yl)ethyl]-4-piperidyl]-2-methyl-1H-indole, 24c, Mp: 182° C.

PHARMACOLOGICAL TESTS

The compounds of the invention were tested in well recognized and reliable methods. The tests were as follows and the results are given in the following Tables I and II.

QUIPAZINE INHIBITION

Quipazine is a 5-HT$_2$ agonist, which induces head twitches in rats. The test is a test for 5-HT$_2$-antagonistic effect testing the ability to inhibit head twitches. The method and test results for some reference substances are published by Arnt et al. (*Drug Development Research*, 16, 59–70, 1989).

Procedure

Test substance is injected s.c. 2 hrs before or p.o. 24 hrs before quipazine administration (6.8 mg/kg, s.c., dimaleate). Four rats, male Wistar (Mol:Wist) SPF rats weighing 170–240 g, are used at each dose level. A control group is included each test day. By repeated testing (2, 24 hrs) the control group is the same, however. After quipazine administration the rats are individually placed in the observation cages and head twitches are counted in an observation period of 30–40 min. after injection of quipazine.

Total number of head twitches in each group is calculated and the result for each dose is expressed as per cent of the response in the control group. ED$_{50}$ values are calculated by log-probit analysis. The test must be repeated if the average number of head twitches is lower than 9 in the control group.

ANTAGONISM OF PERGOLIDE-INDUCED CIRCLING BEHAVIOUR IN RATS WITH UNILATERAL 6-OHDA LESIONS

Dopamine (DA) D-2 agonists induce contralateral circling behaviour in rats with 6-OHDA lesions. Pergolide-induced circling is antagonized by DA D-2 antagonists. (Arnt,J. and J. Hyttel, *Eur. J. Pharmacol.* 102, 349–354, 1984; Arnt, J. and J. Hyttel, *J. Neural. Transm.* 67, 225–240, 1986).

Procedure

Male Wistar rats (Mol:Wist) weighing about 200 g at the time of operation are used. Unilateral lesions are made in pentobarbital anaesthetized rats by injection of 6-OHDA. HCl 9.7 µg/µl (equivalent to 8 µg free base) per 4 min. into the rostral tip of the substantia nigra. The saline solution contains ascorbic acid 0.2 mg/ml, is bubbled with $N_2$ and is kept ice-cold. The experiments are done when stable contralateral circling responses to pergolide (0.05 µmol/kg, s.c.) are obtained. The circling response is measured in rotometer bowls. Only rats showing more than 400 complete turns in 2 hrs control session are used. Dose-response curves are obtained by alternating test and control sessions on a weekly basis. The antagonists are injected s.c. 2 hrs before the agonist. The effect of individual doses of test drugs is calculated as per cent of the mean effect of control sessions one week before and one week after the test session for each rat. ED$_{50}$ values are calculated by log-probit analysis. Four to eight rats are used at each dosage.

INHIBITION OF $^3$H-PRAZOSIN BINDING TO $\alpha_1$ ADRENOCEPTORS IN RAT BRAIN IN VITRO By this method the inhibition of the binding of $^3$H-Prazosin (0.25 nM) to $\alpha_1$ adrenoceptors in membranes from rat brain is determined in vitro. Method and results in Hyttel and Larsen, *J. Neurochem*, 44, 1615–1622, 1985; Skarsfeldt and Hyttel, *Eur. J. Pharmacol.* 125, 323–340, 1986.

Procedure

Male Wistar (Mol:Wist) rats (125–200 g) are sacrificed and brain tissue is dissected and weighed. The tissue is homogenized (Ultra Turrax, 10 sec.) in 10 ml of ice-cold 50 nM Tris buffer pH 7.7 (at 25° C.). The homogenate is centrifuged twice at 20,000 g for 10 min. at 4° C. with rehomogenization of the pellet in 10 ml ice-cold buffer. The final pellet is homogenized in 400 vol (w/v) ice-cold buffer.

Incubation tubes kept on ice in triplicate receive 100 µl of drug solution in water (or water for total binding) and 4000 µl of tissue suspension (final tissue content corresponds to 10 mg original tissue). The binding experiment is initiated by addition of 100 µl of $^3$H-Prazosin (final concentration 0.25 nM) and by placing the tubes in a 25° C. water bath. After incubation for 20 min. the samples are filtered under vacuum (0–50 mBar) through Whatman GF/F filters (25 mm). The tubes are rinsed with 5 ml ice-cold buffer which then are poured on the filters. Thereafter, the filters are washed with 5 ml of buffer. The filters are placed in counting vials and 4 ml of appropriate scintillation fluid (e.g. Picofluor TM 15) are added. After shaking for 1 h and storage 2 hrs in the dark the content of radioactivity is determined by liquid scintillation counting. Specific binding is obtained by subtracting the nonspecific binding in the presence of 1 µM of Prazosin.

For determination of the inhibition of binding five concentrations of drugs covering 3 decades are used.

The measured cpm are plotted against drug concentration on semilogarithmic paper and the best fitting S-shaped curve is drawn. The $IC_{50}$ value is determined as the concentration at which the binding is 50% of the total binding in control samples minus the nonspecific binding in the presence of 1 µM of Prazosin. $^3$H-Prazosin=[furoyl-5-$^3$H]-Prazosin from New England Nuclear, specific activity approximately 20 Ci/mmol.

INHIBITION OF $^3$H-KETANSERIN BINDING TO SEROTONIN $S_2$ (5-HT$_2$) RECEPTORS IN RAT CORTEX IN VITRO

By this method the inhibition by drugs of the binding of $^3$H-Ketanserin (0.5 nM) to Serotonin $S_2$ (5-HT$_2$) receptors in membranes from rat is determined in vitro. Method in Hyttel, *Pharmacology & Toxicology*, 61, 126–129. 1987.

Procedure

Male Wistar (Mol:Wist) rats (125–250 g) are sacrifices and cortical tissue is dissected and weighed. The tissue is homogenized (Ultra Turrax, 10 sec.) in 10 ml of ice-cold 50 mM tris buffer pH 7.7 (at 25° C.). The centrifuge glassware used in this step has been rinsed by sonication for 10 min. in ethanol. The homogenate is centrifuged twice at 20,000 g for 10 min. at 4° C. with rehomogenization of the pellet in 10 ml ice-cold buffer. The final pellet is homogenized in 500 vol (w/v) ice-cold buffer.

Incubation tubes kept on ice in triplicate receive 100 µl of drug solution in water (or water for total binding) and 2000 µl of tissue suspension (final tissue content corresponds to 4 mg original tissue). The binding experiment is initiated by addition of 100 µl of $^3$H-Ketanserin (final concentration 0.5 nM) and by placing the tubes in a 37° C. water bath. After incubation for 30 min. the samples are filtered under vacuum (0–50 mBar) through Whatman GF/F filters (25 mm). The tubes are rinsed with 5 ml ice-cold buffer which are then poured on the filters. Thereafter, the filters are washed with 2×5 ml of buffer. The filters are placed in counting vials and 4 ml of appropriate scintillation fluid (e.g., Picofluor TM 15) are added. After shaking for 1 h and storage 2 hrs in the dark the content of radioactivity is determined by liquid scintillation counting. Specific binding is obtained by subtracting the nonspecific binding in the presence of 1 µM mianserin. For determination of the inhibition of binding five concentrations of drugs covering 3 decades are used.

The measured cpm are plotted against drug concentration on semilogarithmic paper and the best fitting S-shaped curve is drawn. The $IC_{50}$ value is determined as the concentration at which the binding is 50% of the total binding in control samples minus the nonspecific binding in the presence of 1 µM mianserin.

$^3$H-Ketanserin=[ethylene-$^3$H]-ketanserin hydrochloride from New England Nuclear, specific activity 60–80 Ci/mmol.

INHIBITION OF $^3$H-SPIPERONE BINDING TO DOPAMINE D-2 RECEPTORS IN RAT CORPUS STRIATUM IN VITRO

By this method the inhibition by drugs of the binding of $^3$H-spiperone (0.5 nM) to dopamine D-2 receptors in membranes from rat corpus striatum is determined in vitro. Method and results in Hyttel and Larsen, *J. Neurochem*, 44, 1615–1622, 1985).

Procedure

Male Wistar (Mol:Wistar) rats (125–250 g) are sacrificed and striatal tissue is dissected and weighed. The tissue is homogenized (Ultra Turrax, 10 sec.) in 10 ml of ice-cold 50 mM K-phosphate buffer pH 7.4 (at 25° C.). The homogenate is centrifuged twice at 20,000 g for 10 min. at 4° C. with rehomogenization of the pellet in 10 ml ice-cold buffer. The final pellet is homogenized in 1300 vol (w/v) ice-cold buffer.

Incubation tubes kept on ice in triplicate receive 100 µl of drug solution in water (or water for total binding) and 4000 µl of tissue suspension (final tissue content corresponds to 3.08 mg original tissue). The binding experimental is initiated by addition of 100 µl of $^3$H-spiperone (final concentration 0.5 nM) and by placing the tubes in a 37° C. water bath. After incubation for 10 min. the samples are filtered under vacuum (0–50 mBar) through Whatman GF/F filters (25 mm). The tubes are rinsed with 5 ml ice-cold buffer which are then poured on the filters. Thereafter, the filters are washed with 2×5 ml of buffer. The filters are placed in counting vials and 4 ml of appropriate scintillation fluid (e.g. Picofluor TM 15) are added. After shaking for 1 h and storage 2 hrs in the dark the content of radioactivity is determined by liquid scintillation counting. Specific binding is obtained by subtracting the nonspecific binding in the presence of 10 µM of 6,7-ADTN.

For determination of the inhibition of binding five concentrations of drugs covering 3 decades are used.

The measured cpm are plotted against drug concentration on semilogarithmic paper and the best fitting S-shaped curve is drawn. The $IC_{50}$ value is determined as the concentration at which the binding is 50% of the total binding in control samples minus the nonspecific binding in the presence of 10 µM of 6,7-ADTN. $^3$H-Spiperone=[phenyl-4-$^3$H]-spiperone from Amersham International plc. England, specific activity 15–25 Ci/mmol.

TABLE I

Pharmacological activity of 6-substituted or 2-alkyl substituted 1-arylindoles and 1-aryl-2,3-dihydroindoles In vitro.

| Compound No. | Binding ($IC_{50}$ nM) | | |
| --- | --- | --- | --- |
| | $^3$H Ket. | $^3$H Spi. | $^3$H Praz. |
| 2a | 3.5 | 66 | 55 |

TABLE I-continued

Pharmacological activity of 6-substituted or 2-alkyl substituted 1-arylindoles and 1-aryl-2,3-dihydroindoles In vitro.

| Compound No. | Binding (IC$_{50}$ nM) | | |
|---|---|---|---|
| | $^3$H Ket. | $^3$H Spi. | $^3$H Praz. |
| 2b | 1.9 | 67 | |
| 4a | 1.5 | 130 | 70 |
| 4b | 1.4 | | |
| 4c | 2.9 | 280 | 91 |
| 4d | 1.7 | | |
| 4e | 2.8 | 300 | 49 |
| 4f | 11 | | |
| 4g | 0.8 | 270 | 24 |
| 4h | 1.8 | | |
| 4i | 7.1 | 710 | 140 |
| 4j | 40 | 1100 | |
| 4k | 9.0 | 600 | |
| 5a | 1.6 | 190 | 85 |
| 5b | 2.0 | | |
| 5c | 16 | 2000 | 730 |
| 5d | 18 | | |
| 5e | 3.4 | | |
| 5f | 3.5 | | |
| 5g | 3.2 | | |
| 5h | 1.2 | | |
| 5i | 8.6 | 1100 | |
| 5j | 13 | 1500 | |
| 6a | 2.7 | 81 | |
| 6b | 2.7 | 180 | 76 |
| 9a | 1.8 | 300 | 76 |
| 9b | 2.6 | | |
| 9c | 12 | | |
| 9d | 1.9 | 150 | |
| 9e | 6.4 | | |
| 9f | 2.5 | | |
| 9g | 6.2 | | |
| 9h | 1.6 | | |
| 9i | 2.2 | | |
| 9j | 11 | | |
| 9k | 4.0 | | |
| 9l | 1.3 | | |
| 12a | 6.2 | | |
| 13a | 4.4 | 270 | 110 |
| 15a | 2.0 | 500 | 120 |
| 15b | 6.7 | 2500 | |
| 15c | 2.6 | 1000 | 330 |
| 15d | 9.3 | 4500 | |
| 15e | 7.6 | 3500 | |
| 15f | 2.5 | 730 | 370 |
| 15g | 11 | 3200 | 670 |
| 15h | 6.0 | 620 | 450 |
| 15i | 150 | 3200 | |
| 15j | 3.7 | 300 | 120 |
| 15k | 4.5 | | |
| 15m | 4.4 | 410 | |
| 17a | 4.6 | | |
| 18a | 2.5 | | |
| 19a | 3.2 | | |
| 20a | 5.3 | 180 | |
| 21a | 9.6 | | |
| 24b | 1.0 | | |
| 24c | 0.69 | 380 | 61 |
| ritanserin | 0.40 | 12 | 47 |
| ICI 169369 | 15 | 490 | 300 |
| sertindole (Lu 23-174) | 0.72 | 4.1 | 3.4 |
| Lu 21-152 | 1.4 | 2.6 | 7.6 |

TABLE II

Pharmacological activity of 6-substituted or 2-alkyl substituted 1-arylindoles and 1-aryl-2,3-dihydroindoles In vivo

| Compound No. | Quipazine inhibition ED$_{50}$ ($\mu$mol/kg) | | Pergolide rot. inhibition |
|---|---|---|---|
| | 2h (sc) | 24h (po) | 2h (sc) |
| 4a | 0.11 | 0.06 | >17 |
| 4b | 0.06 | | >23 |
| 4g | 0.02 | 0.04 | >24 |
| 5a | 0.04 | 0.11 | >18 |
| 5f | 0.12 | 0.04 | >42 |
| 6b | 0.04 | | |
| 9b | 0.12 | <0.14 | |
| 15a | 0.01 | | |
| 15j | 0.08 | | |
| 20a | 0.49 | | |
| ritanserin | 0.08 | 0.98 (sc) | >21 |
| ICI 169369 | >3.6 | nt | nt |
| sertindole (Lu 23-174) | 0.04 | 0.04 | 7.2 |
| Lu 21-152 | 0.02 | 0.15 (sc) | 0.02 | nt: Not tested.

From the in vitro data in Table I it is evident that the novel indole and 2,3-dihydroindole derivatives in general potently bind to 5-HT$_2$ receptors with nanomolar affinities. The corresponding 5-substituted indoles as disclosed by U.S. Pat. No. 4,710,500 also have high affinities for 5HT$_2$ receptors. Lu 21-152 (1-(4-fluorophenyl)-3-[4-(2-hydroxyethyl)-1-piperazinyl]-5-trifluoromethyl-1H-indole) and sertindole (Lu 23-174 (5-chloro-1-(4-fluorophenyl)-3-[1-[2-(2-imidazolidinon-1-yl)ethyl]-4-piperidyl]-1H-indole)) are shown as examples of such 5-substituted derivatives. By introducing suitable substituents into the 6-position or suitable alkyl substituents into the 2-position of the indole or 2,3-dihydroindole ring it appears from Table I that the in vitro affinity for central dopamine D-2 and central noradrenergic $\alpha_1$ receptors is strongly attenuated. Selectivity ratios of D-2/5-HT$_2$ receptor affinities better than about 20 and ratios of $\alpha_1$/5-HT$_2$ receptor affinities better than about 20 and even for most compounds better than 100 and 50 respectively, are obtained, which is at least as good as ratios obtained for the standard 5-HT$_2$ antagonists ritanserin and ICI 169369. From the data presented in Table II (quipazine inhibition) it is evident that the novel indole compounds have potent central 5-HT$_2$ antagonism with good oral bioavailability and long duration of action. However, contrary to the 5-substituted indoles disclosed by U.S. Pat. No. 4,710,500, which were also potent central 5-HT$_2$ antagonists in vivo, the novel 6-substituted derivatives of this invention show no central antidopaminergic activity in vivo as measured by the inhibition of pergolide induced rotations in rats with unilateral 6-OHDA lesions (Table II), which test is a extrremely sensitive test for dopamine D-2 antagonistic activity in vivo (Arnt, J. and J. Hyttel, *J. Neural. Transm.* 67, 225–240, 1986).

FORMULATION EXAMPLES

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilization of the solution and filling in suitable ampules or vials. Any suitable additive conventionally used in the art may be added, such as tonicity agents, preservatives, antioxidants, etc.

Typical examples of recipes for the formulations of the invention are as follows:

1) Tablets containing 5 milligrams of Compound 5a calculated as the free base:

| Comp. 5a | 5 mg |
|---|---|
| Lactose | 18 mg |
| Potato starch | 27 mg |
| Sucrose | 58 mg |
| Sorbitol | 3 mg |
| Talcum | 5 mg |
| Gelatine | 2 mg |
| Povidone | 1 mg |
| Magnesium stearate | 0.5 mg |

2) Tablets containing 50 milligrams of Compound 4a calculated as the free base:

| Comp. 4a | 50 mg |
|---|---|
| Lactose | 16 mg |
| Potato starch | 45 mg |
| Sucrose | 106 mg |
| Sorbitol | 6 mg |
| Talcum | 9 mg |
| Gelatine | 4 mg |
| Povidone | 3 mg |
| Magnesium stearate | 0.6 mg |

3) Syrup containing per milliliter:

| Comp. 5a | 10 mg |
|---|---|
| Sorbitol | 500 mg |
| Tragacanth | 7 mg |
| Glycerol | 50 mg |
| Methyl-paraben | 1 mg |
| Propyl-paraben | 0.1 mg |
| Ethanol | 0.005 ml |
| Water | ad 1 ml |

4) Solution for injection containing per milliliter:

| Comp. 4a | 50 mg |
|---|---|
| Acetic acid | 17.9 mg |
| Sterile water | ad 1 ml |

5) Solution for injection containing per mililiter:

| Comp. 5a | 10 mg |
|---|---|
| Sorbitol | 42.9 mg |
| Acetic acid | 0.63 mg |
| Sodium hydroxide | 22 mg |
| Sterile water | ad 1 ml |

We claim:

1. A substituted indole compound having the formula:

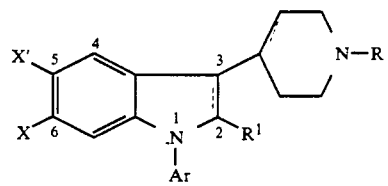

where
Ar is one of a phenyl group, a phenyl group substituted with at least one substituent selected from halogen, lower alkyl, lower alkoxy, hydroxy, trifluoromethyl, and cyano, and a hetero aromatic group selected from 2-thienyl, 3-thienyl, 2-furanyl, 3-furanyl, 2-oxazolyl, 2-imidazolyl, 2-pyridyl, 3-pyridyl, and 4-pyridyl;

each dotted line is an optional double bond;

X is selected from the group consisting of chloro, bromo, iodo, lower alkyl, lower alkoxy, hydroxy, lower alkylthio, lower alkylsulfonyl, lower alkylamino, lower dialkylamino, cyano, trifluoromethyl, and trifluoromethylthio;

X' is selected from the group consisting of hydrogen, halogen, lower alkyl, lower alkoxy, hydroxy, lower alkylthio, lower alkylsulfonyl, lower alkylamino, lower dialkylamino, cyano, trifluoromethyl, and trifluoromethylthio;

$R^1$ is one of hydrogen, lower alkyl and lower alkyl substituted with one or two hydroxy groups;

R is a substituent of the formula

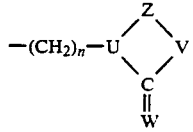

wherein n is an integer from 2–6 inclusive;
W is oxygen or sulfur;
U is nitrogen or carbon;
Z is selected from —CH=CH—, —COCH$_2$—, —CSCH$_2$—, 1,2-phenylene, 1,2-phenylene substituted with halogen or trifluoromethyl, and —(CH$_2$)$_m$—, where m is 2 or 3;
V is selected from oxygen, sulfur, CH$_2$, and NR$^2$, wherein R$^2$ is one of hydrogen, lower alkyl, lower alkenyl, cycloalkyl having three to eight cyclic carbons, cycloalkylmethyl having three to eight cyclic carbons, lower alkyl substituted with one or two hydroxyl groups, and lower alkenyl substituted with one or two hydroxyl groups; and pharmaceutically acceptable acid addition salts or prodrugs thereof.

2. A compound of claim 1, wherein Ar is one of phenyl and phenyl substituted with halogen.

3. A compound according to claim 1, wherein R is a group of the formula:

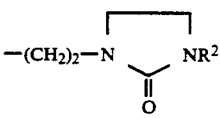

wherein R$^2$ is as defined in claim 1.

4. A compound according to claim 1, wherein X is selected from —Cl, —Br, —CF$_3$, and —CH$_3$ and X' is selected from hydrogen and —Cl.

5. A compound of one of claims 2, 3, or 4, selected from 6-chloro-1-(4-fluorophenyl)-3-[1-[2-[3-(2-propyl)-2-imidazolidinon-1-yl]ethyl]-4-piperidyl]-1H-indole and 1-(4-fluorophenyl)-6-methyl-3-[1-[2-[3-(2-propyl)-2-imidazolidinon-1-yl]ethyl]-4-piperidyl]-1H-indole.

6. A pharmaceutical preparation comprising as active ingredient a compound of claim 1 or a pharmaceutically acceptable acid addition salt or a prodrug thereof in a therapeutically effective amount together with a pharmaceutically acceptable carrier or diluent.

7. A pharmaceutical preparation according to claim 6, comprising a compound of claim 1 in a pharmaceutically acceptable oil.

8. A method for treating at least one of anxiety, depression, sleep disturbance, migraine, negative symptoms of schizophrenia, and Parkinson's disease, comprising the step of administering a therapeutically effective amount of a compound of claim 1.

9. A compound according to claim 1, wherein Ar is 4-fluorophenyl.

10. A compound according to claim 3, wherein R$^2$ is hydrogen or isopropyl.

11. A pharmaceutical preparation according to claim 7, wherein the oil is selected from the group consisting of peanut oil, sesame oil, cotton seed oil, corn oil, soy bean oil, olive oil, and a synthetic ester of a fatty acid or propyleneglycol.

12. A compound of claim 1 selected from the group consisting of:

6-chloro-1-(4-fluorophenyl)-3-[1-[2-[3-(2-propyl)-2-imidazolidinon-1-yl]ethyl]-4-piperidyl]-1H-indole;
6-chloro-1-(4-fluorophenyl)-3-[1-[2-(2-imidazolidinon-1-yl]ethyl]-4-piperidyl]-1H-indole;
1-(4-fluorophenyl)-6-methyl-3-[1-[2-[3-(2-propyl)-2-imidazolidinon-1-yl]ethyl]-4-piperidyl]-1H-indole, and
pharmaceutically-acceptable acid addition salts or prodrugs thereof.

13. A pharmaceutical preparation of claim 6 comprising as active ingredient a compound selected from the group consisting of:

6-chloro-1-(4-fluorophenyl)-3-[1-[2-[3-(2-propyl)-2-imidazolidinon-1-yl]ethyl]-4-piperidyl]-1H-indole;
6-chloro-1-(4-fluorophenyl)-3-[1-[2-(2-imidazolidinon-1-yl]ethyl]-4-piperidyl]-1H-indole;
1-(4-fluorophenyl)-6-methyl-3-[1-[2-[3-(2-propyl)-2-imidazolidinon-1-yl]ethyl]-4-piperidyl]-1H-indole, and
pharmaceutically-acceptable acid addition salts or prodrugs thereof.

14. A method for therapeutical treatment according to claim 8 wherein the compound administered is selected from the group consisting of:

6-chloro-1-(4-fluorophenyl)-3-[1-[2-[3-(2-propyl)-2-imidazolidinon-1-yl]ethyl]-4-piperidyl]-1H-indole;
6-chloro-1-(4-fluorophenyl)-3-[1-[2-(2-imidazolidinon-1-yl]ethyl]-4-piperidyl]-1H-indole;
1-(4-fluorophenyl)-6-methyl-3-[1-[2-[3-(2-propyl)-2-imidazolidinon-1-yl]ethyl]-4-piperidyl]-1H-indole, and
pharmaceutically-acceptable acid addition salts or prodrugs thereof.

* * * * *